(12) United States Patent
Forrester et al.

(10) Patent No.: US 6,944,494 B2
(45) Date of Patent: Sep. 13, 2005

(54) MOTION MEASURING DEVICE

(76) Inventors: Kevin R. Forrester, 1728-22 Avenue N.W., Calgary. Alberta (CA), T2M 1R5; John Tulip, 11625 Edinboro Rd., Edmonton, Alberta (CA), T6G 1Z7; Robert C. Bray, 3639 Utah Dr. N.W., Calgary. Alberta (CA), T2N 4A6

(*) Notice: Subject to any disclaimer, the term of this patent is extended or adjusted under 35 U.S.C. 154(b) by 0 days.

(21) Appl. No.: 10/316,931

(22) Filed: Dec. 12, 2002

(65) Prior Publication Data

US 2003/0120156 A1 Jun. 26, 2003

Related U.S. Application Data

(60) Provisional application No. 60/342,116, filed on Dec. 26, 2001.

(51) Int. Cl.[7] .............................................. A61B 6/00
(52) U.S. Cl. ..................................................... 600/478
(58) Field of Search ........................ 600/310, 322–326, 600/330–332, 473, 475–480, 505–509, 407

(56) References Cited

U.S. PATENT DOCUMENTS

| | | | |
|---|---|---|---|
| 4,862,894 A | | 9/1989 | Fujii ............................ 128/666 |
| 4,884,134 A | * | 11/1989 | Tsuji et al. ................... 348/73 |
| 5,163,437 A | | 11/1992 | Fujii et al. ................... 128/665 |
| 5,214,538 A | * | 5/1993 | Lobb ............................ 359/691 |
| 5,240,006 A | | 8/1993 | Fujii et al. ................... 128/665 |
| 5,434,669 A | | 7/1995 | Tabata et al. ................ 356/345 |
| 5,475,420 A | * | 12/1995 | Buchin ......................... 348/72 |
| 5,807,264 A | * | 9/1998 | Paltieli ........................ 600/477 |
| 5,897,494 A | * | 4/1999 | Flock et al. ................. 600/407 |
| 6,159,445 A | * | 12/2000 | Klaveness et al. ........... 424/9.6 |
| 6,588,901 B1 | * | 7/2003 | Grinvald et al. ............ 351/206 |
| 2002/0183601 A1 | | 12/2002 | Tearney et al. |

FOREIGN PATENT DOCUMENTS

| | | | |
|---|---|---|---|
| DE | 3838396 A1 | 5/1990 | ........... G01S/17/88 |
| WO | WO0/236015 A1 | 5/2002 | |

OTHER PUBLICATIONS

Translation of item B1 in the information disclosure statement filed Jun. 19, 2003, namely DE 3838396A1 dated May 17, 1990, inventor Poesl.

Briers, J.D., G.R. Richards, and X.W. He, "Capillary blood flow monitoring using laser speckle contrast analysis (LASCA)" *Journal of Biomedical Optics* 4:1 (1999), Kingston University, United Kingdom, pp. 164–175.

Briers, J.D. and S. Webster, "Quasi real–time digital version of single–exposure speckle photography for full–field monitoring of velocity of flow fields". *Optics Communications* 116 (1995) Kingston University, United Kingdom. pp36–42.

(Continued)

*Primary Examiner*—Francis J. Jaworski

(57) ABSTRACT

Endoscopes are well known devices used for examining surfaces contained within an enclosed cavity. Typical applications for these devices are the examination of tissues within human body cavities or mechanical components contained within engine compartments. An endoscopic apparatus for measuring blood flow contained within an enclosed body cavity is claimed. Such apparatus comprises an electromagnetic radiation source for emitting a coherent beam, an optical relay system for propagating the beam down an endoscopic probe to illuminate a target within an enclosed cavity, an endoscopic optical relay system for capturing the reflected light and transmitting an image of the illuminated region onto the surface of a two-dimensional image sensor, an analog to digital conversion device for capturing analog output signals from the image sensor for conversion to digital format, a display device for immediate visual display of captured images, a method for calculating flow values from a captured digital image containing speckle structure information of the laser illuminated surface, a memory device for storing digital blood flow images, and a display device for immediate visual display of color coded, blood flow images.

21 Claims, 4 Drawing Sheets

OTHER PUBLICATIONS

Dainty, J.C., "Laser Speckle and Related Phenomena", Topics in Applied Physics. 9 (1984) Springer Verlag, New York.

Dunn, A.K., Bolay, H. M.A. Moskowitz, and D.A. Boas. "Dynamic Imaging of Cerebral blood Flow Using Laser Speckle", *Journal of Cerebral Blood Flow and Metabolism* 21 (2001) Lippincott Williams & Wilkins, Philadelphia. pp. 195–201.

Fercher, A.F. and J.D Briers, "Flow visualization by means of a single–exposure photography". *Optics Communications*. 37:5, (1981) pp. 326–380.

Fujii, H., K. Nohira, Y. Yamamoto, H. Ikawa, T. Ohura, "Evaluation of blood flow by laser speckle image sensing", Applied Optics, 26:24 (1987) pp. 5321–5325.

Fukuoka, S., T. Hotokebuchi, K. Terada, N. Kobara, H. Fujii, Y. Sugioka, and Y. Iwamoto, "Assessment of subchondral blood flow in the rabbit femoral condyle using the laser speckle method." *Journal of Orthopaedic Research* 17 (1999) pp. 368–375.

Fukuoka, S., T. Hotokebuchi, S.Jingushi, H. Fujii, Y. Sugioka, and Y. Iwamoto, " Evaluation of blood flow within the subchondral bone of the femoral head: Use of the laser speckle method at surgery for Osteonecrosis." *Journal of Orthopaedic Research* 17 (1999) pp. 80–87.

Konishi, N. and H. Fujii, "Real time visualization of retinal microcirculation by laser flowgraphy." *Optical Engineering* 34:3 (1995) pp. 753–757.

Stern, M.D., "In vivo evaluation of microcirculation by coherent light scattering." *Nature* 254 (1975) pp. 56–58.

Tamaki, Y., M. Araie, E. Kawamoto, S. Eguchi, H. Fujii, "Noncontact, Two–dimensional measurement of retinal micro–circulation using laser speckle phenomenon." *Investigative Ophthalmology & Visual Science* 35:11, (1994) pp. 3825–3834.

European Search Report for EU Patent Application EP 02 02 8357.V. Franz (Munich). Mar. 3, 2003.

* cited by examiner

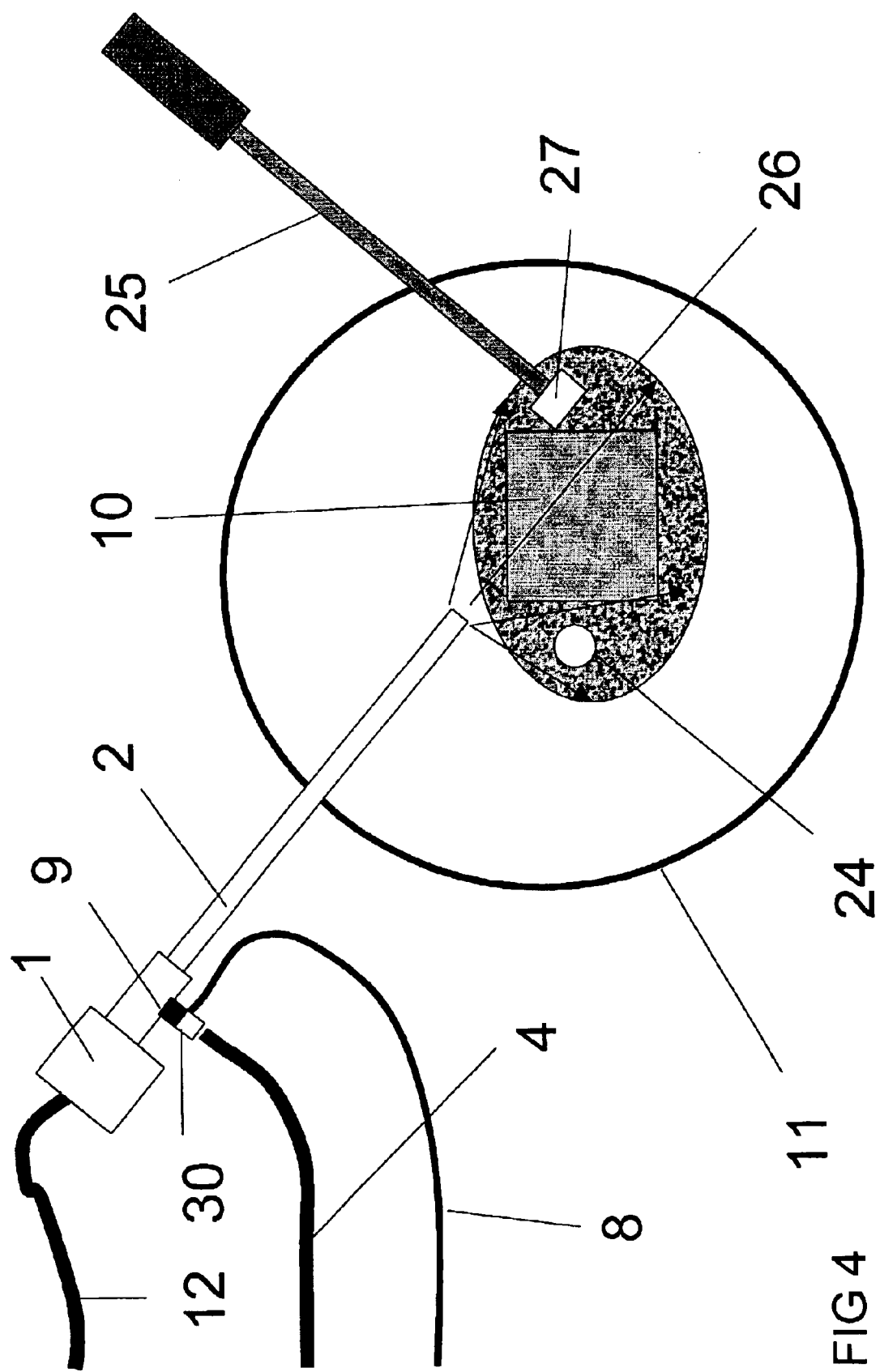

MOTION MEASURING DEVICE

CROSS REFERENCE TO RELATED APPLICATIONS

This application claims the benefit of priority under 35 USC 119(e)(1) of provisional patent application No. 60/342,116 filed Dec. 26, 2001, the content of which is hereby incorporated by reference.

BACKGROUND OF THE INVENTION

This invention relates to a system, method of measurement, and presentation of motion within a cavity, used for example to determine the magnitude of blood perfusion to a tissue located within a body cavity.

When living tissue is illuminated by laser light the light reflected off the natural surface irregularities interferes constructively and destructively producing a random interference pattern called speckle. The speckle pattern produced by a stationary object remains static in time and is said to have a high speckle contrast. If the object contains several individual particles undergoing motion, such as red blood cells, then the phase difference between the interfering beams will change in time. The resulting changes in light intensity reflecting off the tissue can be measured and analyzed to produce an index linearly related to tissue blood flow. Using this principle, Stern et. al. developed a technique for measuring skin blood flow using a collimated laser beam, pinhole aperture and photomultiplier tube (M. D. Stem, "In vivo evaluation of microcirculation by coherent light scattering". *Nature*, 254, pp 56–58, 1975.)

Imaging techniques for mapping tissue blood flow have subsequently evolved from Stem's work and are known in the art as laser speckle methods. Fercher and Briers applied laser speckle using a photographic method for capturing speckle contrast images, an optical filtering technique for mapping retinal vascular structure and a region of tissue fully illuminated by laser light (A. F Fercher and J. D. Briers, "Flow visualization by means of single-exposure photography". *Optics Communications*. 37:5, 326–330, 1981.)

More recently Briers described a speckle imaging method that used a CCD camera and electronic processing rather than photography and optical filtering techniques. He used this method to generate blood flow maps of skin rather than retinal blood flow (J. D. Briers, G. R. Richards, and X. W. He, "Capillary blood flow monitoring using laser speckle contrast analysis (LASCA)", *J. of Biomed. Opt.* 4:1, pp. 164–175, 1999; J. D. Briers, and S. Webster, "Quasi real-time digital version of single-exposure speckle photography for full-field monitoring of velocity or flow fields". *Opt. Comm.* 116, pp 36–42, 1995). A limiting feature of Brier's technique is that the electronic image processing method for determining speckle contrast requires a 7×7 pixel window. This window reduces the original speckle images from 512×512 pixel to 73×73 pixel resolution, resulting in a very low-resolution blood flow map. Another limiting feature is that the Brier contrast method for generating blood flow maps is not a relative measure of blood flow and can only be used to display the sharp contrast between areas of high flow embedded within a stationary or (comparably low flow) surrounding tissue matrix. Although speckle contrast images are useful for displaying tissue vascular structure, they do not provide a clinical technique for the immediate and visual display of "true" blood flow maps, where each pixel within the image is linearly related to blood flow and several images can be captured for the dynamic measurement of relative blood flow and blood flow changes. More recently Dunn and co-workers have used the Brier contrast method to produce cerebral blood flow maps (A. K. Dunn, H. Bolay, M. A. Moskowitz, and D. A. Boas, "Dynamic Imaging of Cerebral Blood Flow Using Laser Speckle". *Journal of Cerebral Blood Flow and Metabolism* 21, 195–201, 2001) where the CCD camera is placed directly above a few millimeters area of surgically exposed cerebral tissue.

Another laser speckle technique is presented in U.S. Pat. No. 4,862,894 and has been specifically applied to the measurement of skin blood flow (H. Fujii, et. al. "Evaluation of blood flow by laser speckle image sensing", *Applied Optics* 26:24, pp. 5321–5325, 1987) and subchondral bone blood flow (S. Fukuoka, T. Hotokebuchi, K. Terada, N. Kobara, H. Fujii, Y. Sugioka, and Y. Iwamoto, "Assessment of subchondral blood flow in the rabbit femoral condyle using the laser speckle method." *J. of Orth. Res.*, 17, pp 368–375, 1999; S. Fukuoka, T. Hotokebuchi, S. Jingushi, H. Fujii, Y. Sugioka, and Y. Iwamoto, "Evaluation of blood flow within the subchindral bone of the femoral head: Use of the laser speckle method at surgery for osteonecrosis." *J. of Orth. Res.*, 17, pp 80–87, 1999). This instrument uses a one-dimensional photo-detector array and a scanning arrangement to produce two-dimensional maps of tissue blood flow rather than a CCD camera. A collimated laser line is projected onto the tissue surface and the resultant line of speckles is simultaneously focused onto the linear CCD device. A time differentiated technique for measuring blood flow is applied rather than the method of measuring speckle contrast so a very fast CCD readout device with consequent low resolution is required. Using the scanning mirror assembly, Fujii and co-workers produce a two-dimensional map of tissue blood flow with a typical pixel resolution of 128×64 (Fuji, 1987). More recently Fujii has replaced the scanning mirror sensor with a high-speed, two-dimensional, image sensor (100×100 pixels) and modified the above time differentiated speckle technique into an ophthalmic device for measuring retinal microcirculation (N. Konishi and H. Fujii, "Real time visualization of retinal microcirculation by laser flowgraphy". *Opt. Eng.* 34, No. 4, pp 753–757, 1995; Y. Tamaki, M. Araie, E. Kawamoto, S. Eguchi, and H. Fujii, "Noncontact, Two-dimensional measurement of retinal microcirculation using laser speckle phenomenon". *Inv. Opth. And Vis. Sci.*, 35, No. 11, pp 3825–3834, 1994). This laser speckle technique is described in U.S. Pat. Nos. 5,163,437 and 5,240,006. It is specifically designed for ophthalmic work and small field of views related to the size of the eye fundus.

No speckle imaging technique described in the cited art is adapted or could be used for endoscopy. A common feature of all of speckle imaging techniques described in the cited art is that they are remote techniques, which require the instrument to be placed directly above or in front of the tissue surface. Remote speckle imaging techniques require fixation of the instrument and the tissue surface. During endoscopic speckle imaging, the surgeon and patient may be expected to move and cause distortion and artifact in the image. Another common feature of prior art speckle imaging techniques is that their image resolution is too low to be useful for clinical endoscopy. Endoscopy is a technique that requires immediate visual display to assist in cavity navigation and tissue recognition, and serious surgical decisions are often made based on what the surgeon "sees". The minimum image resolution required for clinical endoscopy is a standard video resolution of 640×480 pixels. This resolution is maintained for a variable field of view that can range from a few square millimeters to several square centimeters. Prior art speckle-imaging techniques are limited in a low resolution and restricted field of view. Therefore, applying prior art speckle techniques to endoscopy would result in an image that is of too low of resolution or much too small to be clinically useful.

Presently, endoscopic surgery is conducted routinely in hospital operating rooms on a daily basis. Much orthopedic endoscopic surgery is devoted to diagnosis of underlying conditions such as injury, inflammatory arthritis and osteoarthritis. In the surgical art diagnostic information is based on tactile and visual inspection of the tissue through the endoscope. While this information renders data pertaining to the structure of the tissue under examination, it does not provide information about the functional integrity of the tissue structures. Those skilled in the surgical arts would expect the assessment of the metabolic state of tissue physiology in response to injury or inflammation to provide a useful diagnostic. For example such a diagnostic would be useful in determining whether tissue should be repaired or resected when the predicted outcome of healing, based on such endoscopic tactile and visual inspection of tissue anatomy, is uncertain.

Those skilled in the surgical art would expect that measuring tissue temperature could be used to assess the metabolic state of tissue. For example it is well known that the inflammatory response of tissue to injury results in local elevation of tissue temperature. The measurement of tissue temperature in a manner that does not perturb the measurement is problematic. The use of thermometry to assess the metabolic state of tissue has limited clinical relevance because the measurement is local to the point of tissue contact. More recently the methods of thermography have been used to assess tissue metabolic state, in particular for the diagnosis on malignancy. This method relies upon the imaging of mid infrared radiation emitted for tissue. Mid infrared radiation will not transmit through the materials of the imaging optics used in endoscopes so the use of thermography in combination with an endoscope is not possible.

SUMMARY OF THE INVENTION

In this patent, we disclose a method for endoscopic tissue diagnosis, which makes use of blood perfusion as a secondary indicator of tissue metabolism. The inventors have demonstrated a high degree of correlation between blood perfusion and the predicted outcome of healing. There are both high and low thresholds in blood flow, which predict the potential for the healing of connective tissues. For example the determination of whether or not injured meniscus tissue should be repaired or resected, when the predicted outcome of healing based on tactile and visual inspection of tissue anatomy alone is uncertain, may be made using endoscopic imaging of blood perfusion. The methods of endoscopic blood perfusion imaging disclosed in this patent may be used as a surgical guide. In the event that an inadequate vascular response indicates poor healing, the degree of resection and the margin of resection when removing tissue that are avascular and non-viable are determined from the perfusion image. In general, in orthopedic surgery, a tissue perfusion image, which shows regions of low metabolic state of tissue physiology, is useful in determining conservative surgical resection margins. Conservative surgery may result in improved preservation of mechanical load bearing function of an injured joint.

In the present invention the limitations of prior art speckle imaging are overcome and a method of clinical endoscopic speckle imaging of blood flow is disclosed.

An embodiment of an apparatus according to the invention for example comprises a laser arranged to illuminate a body cavity, a device arranged to provide endoscopic imaging of laser-illuminated tissue and an image analyzer and display. Light from the laser source is guided to the tissue surface using a light guide, and laser light exiting this light guide produces a substantially uniform and bright illumination of the target tissue to enable effective speckle imaging through an endoscope.

In one aspect of the invention, speckle from the target tissue is imaged using an endoscope and camera, preferably the same endoscope and standard camera that are used for surgery. Image processing methods are applied to speckle images, captured by the endoscopic camera, so as to create blood flow images.

Such image processing methods enable fast acquisition of blood flow images to minimize movement artifact that might be normally associated with endoscopic surgery.

In another aspect of the invention, such image processing methods are applied to the speckle images so as to enable one to one pixel correspondence with the standard color video used for surgery thus permitting identification of blood flow in anatomical features and boundaries of the tissue.

In another aspect of the invention, such image processing methods are applied to speckle images so as to enable the generation of blood flow images linearly related to tissue blood flow.

In another aspect of the invention, such image processing utilizes averaging techniques and artifact movement recognition software to enhance blood flow image quality and eliminate movement artifact that is not associated with tissue blood flow.

These and other aspects of the invention are described in the detailed description and claimed in the claims that follow.

BRIEF DESCRIPTION OF THE DRAWINGS

There will now be described preferred embodiments of the invention, with reference to the drawings, by way of illustration, in which like numerals denote like elements and in which:

FIG. 4 is a detailed schematic of the method for illuminating the target region and technique for eliminating motion artifact.

DETAILED DESCRIPTION OF PREFERRED EMBODIMENTS

Comprising is used in the claims in its non-exclusive sense. The indefinite article "a" or "an" before an element when used in the claims does not exclude the possibility that more than one of the element is present. The term light means all possible frequencies of electro-magnetic radiation having utility for motion detection, as for example within a human body, the term laser means all forms of coherent light sources suitable for use in endoscopic work, and the term electronic camera means all forms of two-dimensional, electromagnetic radiation receiving arrays suitable for receiving light emitted by a laser.

Figure 1:
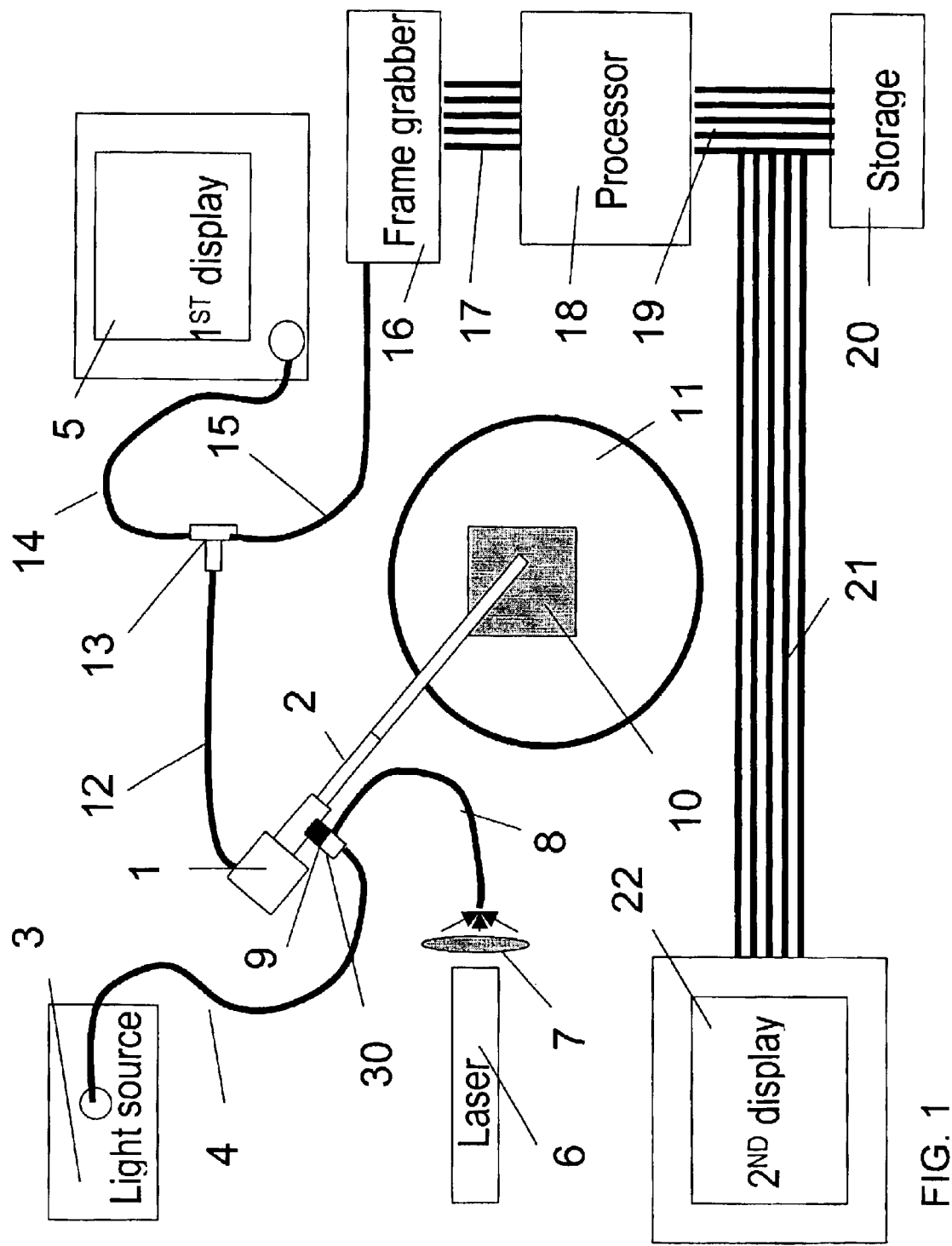
FIG. 1 shows an overall schematic of the manner for imaging tissue blood flow using endoscopic methods.
Figure 2:
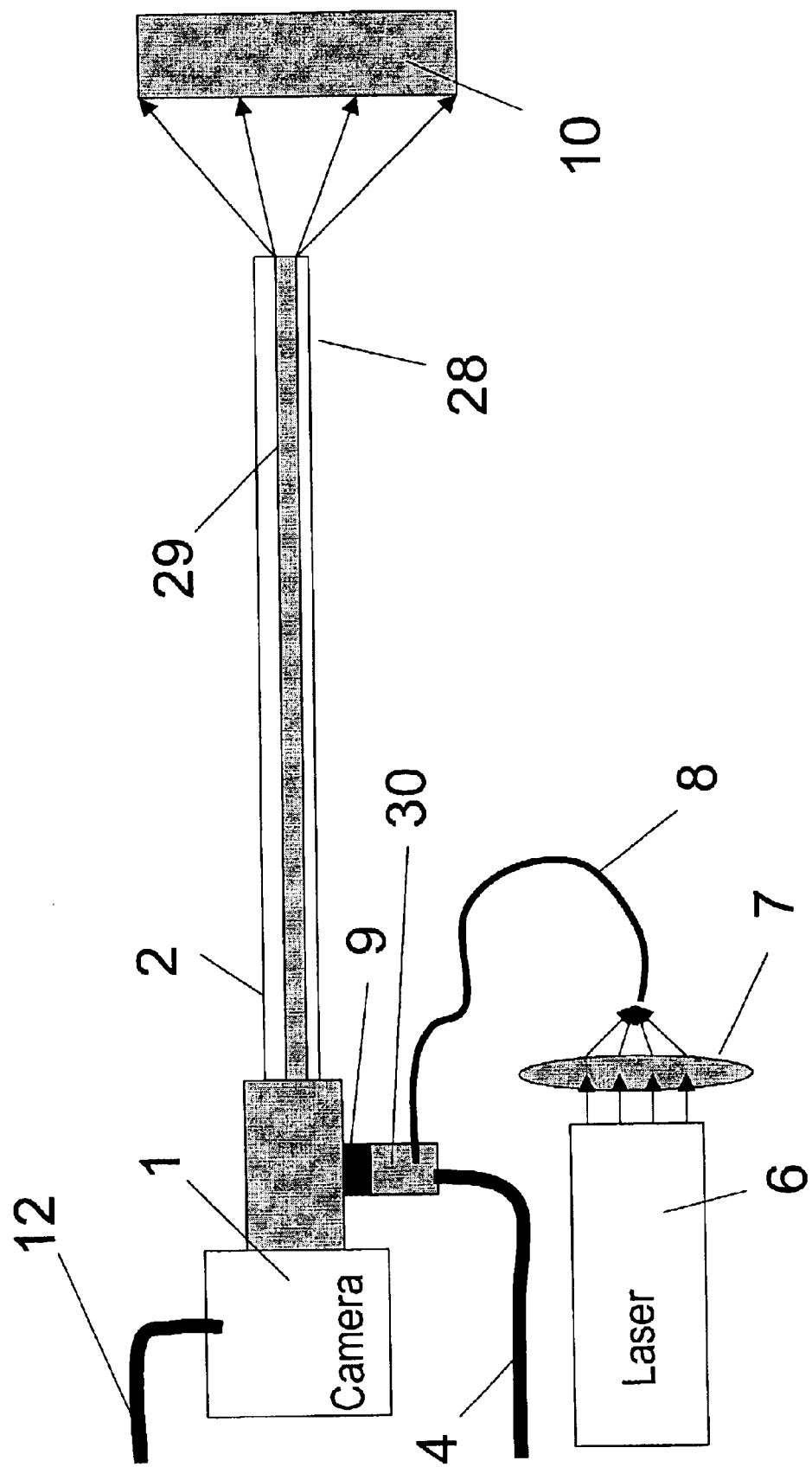
FIG. 2 is a detailed schematic of the endoscopic device and preferred embodiment for the endoscope light guide method of guiding the laser light to the tissue surface.

Referring to FIG. 1 and FIG. 2, an exemplary endoscopic motion measurement device makes use of much of existing endoscopic hardware consisting of: camera 1, endoscope shaft 2 containing imaging relay lens system 29 and internal light guide 28, standard object illumination white light source 3, light-guide 4 for delivering white light from source to endoscope internal light guide entrance port 9, and video display components 5.

For flow or motion measurements using the methods claimed here, sensitivity to low flow and range of measurement is maximized when the laser source is highly polarized and monochromatic. This is because polarized monochromatic light sources produce the highest speckle contrast in images of stationary objects. Standard endoscopic procedures use non-polarized, white light sources, where polarization and mode preservation of the source light is not necessary. Thus, the source light guide 4 and endoscopic internal light guide 28 on standard endoscopes may consist of one or several multimode fiber optic cables that do not necessarily preserve the light mode quality. As a result, light mode and polarization degrades as a function of traveling distance through these light guides, preventing a proper blood flow measurement. However, it is favorable to utilize as much of the standard endoscopic equipment as is possible because it minimizes modification to the surgical procedure.

We have determined that most standard white light source guides 4 consist of a fiber-bundle of several meters length that result in too much mode degradation for proper blood flow measurement. However, the endoscopic shaft 2 containing the internal light guide 28 in most standard endoscopes is of a short enough length that polarization and mode degradation of the source light does not degrade significantly and blood flow measurement is possible. Thus, the preferred embodiment of the method for guiding laser light to the distal tip of the endoscope to illuminate tissue of interest 10 uses internal light guide 28 contained within endoscope shaft 2.

FIG. 2 is a detailed schematic demonstrating the method of laser light transmittance to the tissue of interest for the preferred embodiment of the instrumentation shown in FIG. 1. Modification to the standard light delivery hardware includes a laser light delivery system including; laser transmitter 6 and lens arrangement 7 for coupling laser light to fiber optic cable 8 for delivering laser light to the endoscope internal light guide 28, and optical or mechanical switching device 30 for switching optical connection of laser source fiber 8 and white light source fiber 4 to endoscope light guide entrance port 9.

Figure 3:
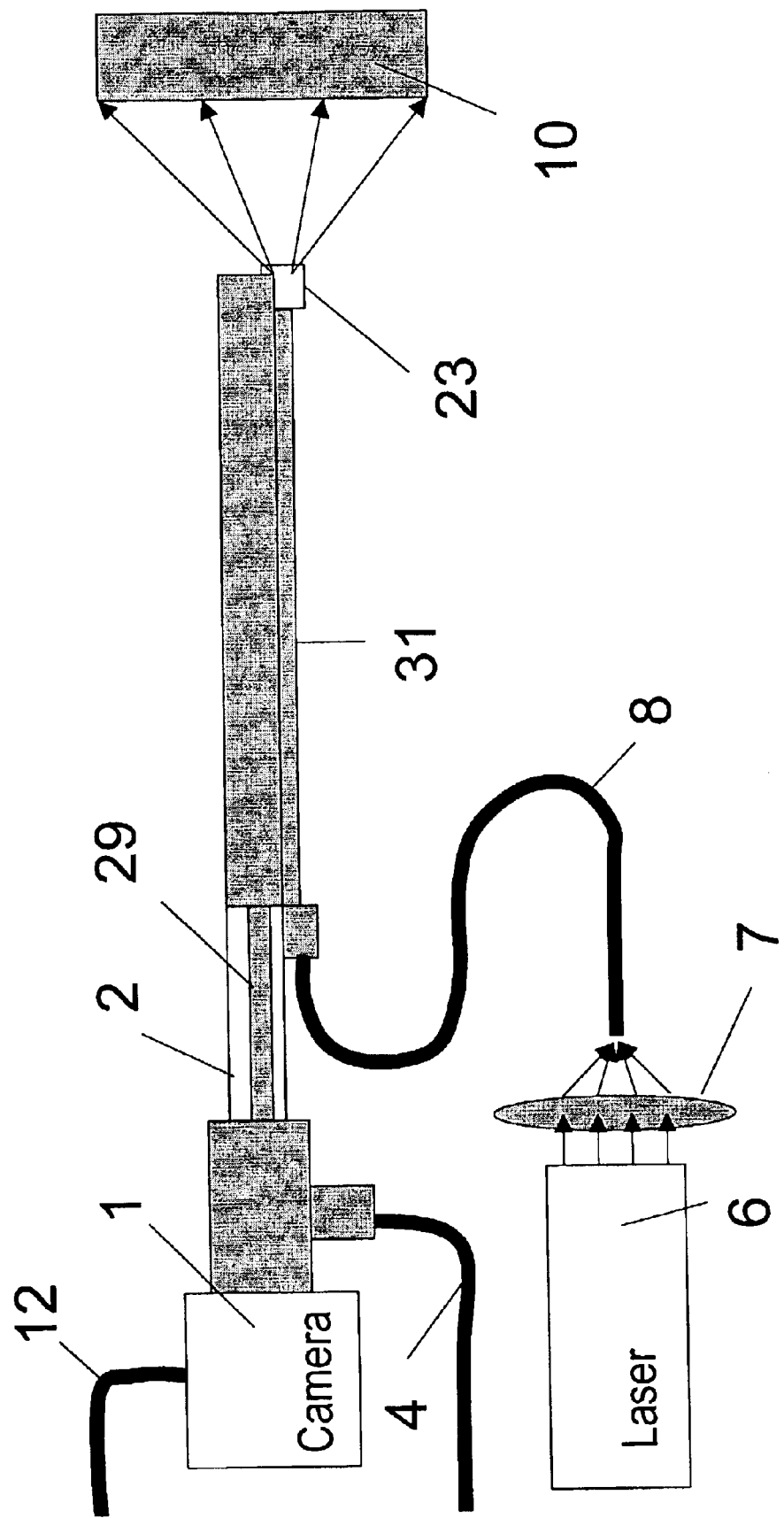
FIG. 3 is a detailed schematic of the endoscopic device and alternate embodiment for the endoscope light guide method of guiding the laser light to the tissue surface.

An alternate embodiment of the method of laser light delivery to the distal tip of the endoscope is given in FIG. 3. The laser light output from the transmitter 6 is focused into a fiber optic cable 8 using an optical arrangement 7. The fiber optic cable delivers the laser light to the endoscope system by fitting down the smaller barrel of a double-barreled, steel sleeve 31. The endoscope shaft 2 containing relay lens arrangement 29 slides into the larger barrel of sleeve 31 such that the objective lens of the endoscopic relay lens system 29 has access to the tissue of interest 10. The smaller barrel of sleeve 31 is used for structure and for guiding fiber optic cable 8 to the distal tip of the endoscope system, maintaining a similar optical axis between the laser light delivery system and the relay lens light capture system of the standard endoscope hardware. The distal tip of the smaller fiber optic barrel of sleeve 31 contains an optical arrangement 23 comprising of lenses and prisms designed to expand the diverging laser light exiting the fiber and to correct for any deviations in the optical axes of the fiber optic laser light delivery system 8 and optical image collection system 29. This ensures a full and uniform laser illumination of tissue 10 within the camera field-of-view. Depending on the blood flow range and sensitivity required by the measurement, fiber optic light delivery system 8 may consist of various combinations of single or bundled multimode or single mode, polarization maintaining, or non-polarization maintaining fiber optic cables.

In the preferred embodiment of the instrument shown in FIGS. 1 and 2, images of laser illuminated tissue are captured using much of the standard endoscope hardware including; imaging relay lens system 29 contained within endoscope shaft 2 for optical transfer of laser illuminated tissue images to camera focal plane, camera for electronic capture of laser illuminated tissue 1, and electronic cable 12 for transferring video signals to video monitor system 5 ($1^{st}$ display).

Modifications to the standard hardware for transfer of video signals include; video signal 1-to-2 channel splitter 13, for splitting channel 12 containing video signal output from camera 1 into 2 channels, 14 and 15, where channel 14 feeds the camera video signal to a standard endoscope monitor 5 ($1^{st}$ display) for the real-time, video feed of light-illuminated tissue used by endoscopic surgeons for maneuvering about the joint cavity and channel 15 for transferring camera video signal to a frame grabber card 16.

The frame grabber card 16 digitizes analog video signals and digital data is transferred to a computer processing system 18, via digital, data-transfer bus 17. Digitized, laser-illuminated images are processed by computer processing system 18 into blood flow images using a speckle reduction and comparison method for generating images containing blood flow information, which includes the steps of: capturing a sequence of speckle images of laser illuminated tissue; comparing these speckle images to a reference image that is an image of the illuminated tissue where speckle has been reduced; and representing information obtained from this comparison in image format such that images are generated with a relation to blood flow. The speckle reduction and comparison method is described in more detail below starting in paragraph 36. Images are transferred to digital storage medium 20 via data transfer bus 19. Images are also transferred to monitor 22 ($2^{nd}$ display) for real-time, immediate display of processed, blood flow images via data bus 21.

In an alternate embodiment of the method for image capture the standard endoscope camera is replaced by a high resolution, scientific quality digital camera with associated analog to digital conversion hardware. Digital output is then fed directly to the computer processing system 18 for processing, storage, and display of blood flow and laser speckle images.

When an object surface has a roughness of less than one wavelength, the light field at the diffraction plane has a non-vanishing specular component superimposed with a fluctuating diffuse component. For measurements in tissue, the diffuse component originates from tissue scattering points below the surface and is the fluctuating light component leading to the speckle pattern. This is the light component that carries information of blood flow and, in cases when the tissue surface is very smooth, can be relatively weak compared to the specular component.

Internal body tissue can be very smooth, having a high specular light component when illuminated. Therefore, it is effective for a blood perfusion imager to use a technique to eliminate or reduce the specular component in the measured light reflected back from the tissue surface. A further embodiment of the invention uses a polarization technique to reduce specular reflection such that a polarized light source is used in conjunction with a polarization filter with the polarization axis aligned perpendicular to the polarization axis of the illuminating light. This filter can be placed at any location within the light receiving optics of the endoscopic imaging relay lens system 29.

In the preferred embodiment of the method of light delivery, polarization of the light source can be achieved by attaching a polarization filter over the internal light guide exit port located at the distal tip of the endoscope. This filter must not cover the light receiving optics also located at the distal tip of the endoscope shaft. For most standard endoscopes, this requires a ring shaped design. Alternatively, a circular polarization filtering technique can be used with a polarization filter and quarter wave-plate located at the distal tip of the endoscopic device.

In the alternate embodiment of the method of light delivery, a polarized laser source can be used with a single mode, polarization maintaining fiber optic for fiber optic cable 8, eliminating the need for a polarization filter placed over the source light.

For some measurements, surface reflection does not present a significant problem or motion of the object surface itself is desired. Therefore, this endoscopic "cross polarization" technique is optional and can be used to reduce surface reflections when sub-surface diffuse light is the desired scattered light component.

For optical perfusion measurements using coherent light sources it may be necessary to reduce non-coherent background light from the measurement. The simplest method would be to remove all ambient light sources during a measurement. However, during endoscopic surgery it may be difficult to remove all ambient surgical light while a blood flow measurement is performed. Therefore, a further embodiment of the invention uses a narrow band-pass filter, of 3–10 nm wavelength range, centered on the source wavelength and placed within the endoscopic imaging relay lens system 29 for effectively reducing ambient light during endoscopic blood flow measurement.

Endoscopic blood flow applications include but are not limited to measurement in an abdominal cavity, a joint cavity, a pulmonary cavity, and a bladder.

A speckle reduction and comparison method for generating relative blood flow images from laser speckle images will now be described. The blood flow algorithms described in this method can be used to measure motion of any object including and not limited to blood flow and bio-activity, where bioactivity applications include and are not limited to measuring the ripeness of fruit and vegetables, the vitality of live tissue and to ascertain the time of death for dead tissue. Various modifications could be made to the algorithms and mechanical methods used to perform a speckle reduced, reference image technique for generating blood flow images through the analysis of laser speckle images captured using a two dimensional detector with a finite integration time.

This method can be used for any instrument using a two-dimensional photo-detector and focusing lens arrangement, endoscopic or otherwise. For example, an electronic camera attached to any focusing lens arrangement, including but not limited to: a boroscope lens system for measuring motion of mechanical parts within mechanical cavities, a microscope arrangement for measuring microscopic motion including microvascular blood flow, a video lens for measuring larger objects such as areas of exposed tissue including organs and body parts, a close focus zoom lens for measuring smaller objects such as regions of exposed tissue, an opthalmoscope for measuring retinal blood flow, and a zoom lens for measuring motion in distant objects. The same components shown in FIGS. 1 and 2 would be used, except that the endoscopic components would be replaced with the respective video and light guide systems mentioned here. In FIG. 2, the laser transmitter 6 would be coupled to a suitable light guiding arrangement for uniform illumination of the target 10 instead of fitting to the endoscopic light guide via lens 7, light guide 8 and optical or mechanical switching connection 30. In FIG. 2 the endoscopic light collection system 29 and camera 1 would be replaced by a lens system appropriate for the desired application coupled to a standard electronic camera.

Exemplary calculations used for generating a blood flow image that are disclosed in this patent require capturing an image (or sequence of images) of the tissue of interest while it is illuminated by coherent laser light. The coherent laser light produces a speckle structure in the image of the illuminated tissue. The speckle structures within the tissue image are a random interference pattern created by irregularities on and near the surface of the laser-illuminated tissue. These speckles appear across the tissue image and have a size given by:

$$\sigma \approx 1.2(1+M)\lambda F, \qquad (1)$$

where M is the magnification of the lens, λ is the wavelength of the laser light, and F is the camera F-stop number (A. E. Ennos, edited by J. C. Dainty, In: "Laser Speckle and Related Phenomena", *Topics in Applied Physics*. 9, Springer Verlag, New York, 1984). The independent variables of the above formula are chosen to produce a speckle size on the order of the pixel size in the image. This is to ensure that the statistics performed on the image pixels is as close as possible to the statistics for the speckle theory.

The speckle pattern produced by a stationary object remains static in time and contains a distinctive speckle structure. If the object contains several individual particles undergoing motion, such as red blood cells, then the phase difference between the interfering beams will change in time producing a dynamic speckle pattern. If an image of a dynamic speckle structure is captured over a finite integration time then several speckle patterns will become superimposed over one another and the single, well-contrasted speckle pattern becomes destroyed. This relation between motion and the destruction of the speckle pattern over a finite integration time is the basis behind quantifying blood flow, where the extent of destruction depends on the level of flow for the moving red blood cells. Therefore, an image processing method for generating blood flow images as illustrated here requires a method for measuring the level of speckle destruction for each point across the tissue surface. This method uses a speckle reduction technique to generate a speckle-free image of the illuminated tissue that can be used as a reference image to evaluate the speckle structure in the laser-illuminated image. The results of this comparison are then used to quantify motion or flow.

A digital laser speckle image is composed of measured intensities I(x,y), where x and y represent the location of the pixel containing intensity, I. The resolution of the image is determined by the number of rows and columns. A typical video image contains 480 rows and 640 columns, although higher resolution cameras are available. The purpose of these calculations is to maintain the field of view and resolution of the captured video images in the generated blood flow images. This allows the physician to make anatomical comparisons between the blood flow images and the continuous endoscopic video feed. This is desirable in an endoscopic blood flow instrument. Subsequently, the calculations presented here use a high-resolution two-dimensional photo-detector and maintain the resolution in the generated blood flow images. This is different from the prior art, which is either limited to a low-resolution photo-detector (Konishi and Fujii, 1995; Tamaki, et al, 1994; and U.S. Pat. Nos. 5,163,437 and 5,240,006) or use a high-resolution camera but lose the resolution in the generated speckle contrast images (Briers, et al 1999; Briers and Webster, 1995; Dunn et al, 2001). Therefore, prior art LSI techniques result in image resolutions of around 100×100 pixels or less, a resolution far too low to be effective for clinical use.

The exemplary calculations disclosed in this patent use a reference image and comparison technique to produce images of tissue blood flow. This reference image is generated by using a speckle reduction technique to reduce or eliminate the speckle within an image that is otherwise identical to the speckle image produced when tissue is illuminated by highly coherent laser radiation. The level of speckle destruction across a laser illuminated tissue surface can be quantified into a perfusion index linearly related to tissue blood flow using a software technique based on a statistical comparison between the pixels in the speckle reduced, reference image and speckle image captured under coherent laser illumination.

The reference image technique requires capturing or producing an image, where the speckle structure is removed or suitably reduced, $I_{REF}$. This can be achieved either through a mechanical or software method. For example, mechanical methods for generating the reference image can be performed by illuminating the tissue with the same laser light used to capture speckle contrast images but reducing the coherence of the source by vibrating the camera or multi-mode laser fiber during image capture. The amplitude of the vibration must be enough to destroy the speckle structure yet small enough not to destroy the sharpness of the image. Also, the period of the vibration must be several magnitudes smaller than the capture time so as to superimpose several speckle images of various phase differences during image capture. Thus, destroying the speckle structure on the imaged tissue.

Another mechanical method is to illuminate the tissue with a light source of short coherence length. With the proper optical arrangement, the short coherence length source can be made to produce an image identical to the laser-illuminated tissue without the speckle structure. The short coherence length source intensity should illuminate the camera field of view in an identical way as the laser source and is normalized to produce the same detector output current as that produced by the laser-source when temporal or spatial speckle fluctuations are averaged out. One obvious example of a short coherence length source that can be used is the white light source used in standard endoscopes. Another example would be to run the laser used to illuminate the object in a mode that would reduce the coherence length. This can be achieved by using a suitable voltage or current level in the laser driver. Another example would be to introduce a diffusing optical element into the laser source light path.

A software method for producing the reference image is the preferred embodiment presented in this patent.

An exemplary and preferred software method removes the speckle structure using a combined spatial smoothing and time-averaging calculation on each pixel within the captured speckle images:

$$I_{REF}(x, y) = \frac{1}{N_{MAX}} \sum_{N=1}^{N_{MAX}} \left[ \frac{1}{(2i+1)} \sum_{x-i}^{x+i} \left( \frac{1}{(2j+1)} \sum_{y-j}^{y+j} I_{SP,N}(x, y) \right) \right], \quad (2)$$

where $I_{REF}(x,y)$ represents the intensity of the (x,y) pixel in the reference image and $I_{SP,N}(x,y)$ represents the intensity of the (x,y) pixel in the $N^{th}$ speckle image of laser illuminated tissue for a captured sequence of $N_{MAX}$ images and i and j represent the boundaries for a chosen region of pixels surrounding the (x,y) pixel.

Spatial smoothing is an image processing term used for performing an average calculation on each pixel (x,y) using its nearest neighbors. For example, the intensity of the (x,y) pixel within the original speckle image becomes replaced with the average intensity for all of the pixels surrounding the (x,y) pixel within a region defined by horizontal and vertical pixel dimensions of 2i+1 and 2j+1. The size of the region should be several times larger than the dimensions of the speckle to ensure that the speckle spatial frequency will be sufficiently smoothed out in the reference image.

For an object with a dynamic speckle pattern, such as living tissue, the speckle structure can be removed by performing a time averaging over a sequence of $N_{MAX}$ captured speckle images. The order and capture frequency of the speckle images within the sequence is unimportant, as long as the total exposure time for the captured sequence is several times larger than the decorrelation time of the dynamic speckle pattern;

$$T_{SEQ} = N_{MAX} \times T, \quad (3)$$

where T is the camera integration time and $N_{MAX}$ is the number of images in the captured sequence. This will ensure a temporal smoothing of the time averaged speckle image generated from the sequence. For example, bioactivity decorrelates a speckle structure within several milliseconds, which is usually an order of magnitude greater than vascular blood flow. Thus, for living tissue, a captured sequence at standard video rates (30 frames per second) is usually sufficient for a good time average.

Blood flow within a captured speckle image is quantified by performing a sum of difference calculation on the pixels in the captured speckle images $I_{SP,N}$ and the corresponding pixels in the generated reference image, $I_{REF}$;

$$I_{SD}(x, y) = \sum_{N=1}^{N_{MAX}} \left[ \sum_{x-i}^{x+i} \left( \sum_{y-j}^{y+j} |I_{SP,N}(x, y) - I_{REF}(x, y)| \right) \right], \quad (4)$$

where $I_{SD}(x,y)$ is the (x,y) pixel in the sum of difference image, $I_{SD}$, and $N_{MAX}$ is the number of images in the captured sequence.

Higher blood flow will result in a smaller value for $I_{SD}$ (x,y). When the blood flow reaches the maximum value measurable for the chosen camera integration time the speckle image will become completely destroyed and the sum of difference calculation (equation 4) will approach zero. Therefore the blood flow index has an inverse relation to the sum of difference value, $I_{SD}$ (x,y). This value must also be normalized with the total light intensity emitted from the tissue at each location across the image using the reference image, $I_{REF}$ (x,y).

Therefore, the final blood flow image is given by;

$$I_{BF}(x, y) = \sum_{C=0}^{C_{MAX}} A_C \left(\frac{I_{REF}(x, y)}{I_{SD}(x, y)}\right)^C \quad (5)$$

where $I_{BF}(x,y)$ represents the intensity of the (x,y) pixel in the blood flow image, C represents the order of terms in the power series of highest order $C_{MAX}$ of the independent variable that is the ratio of $I_{REF}(x,y)$ and $I_{SD}(x,y)$, and $A_C$ is the constant coefficient for each term.

The number of terms in the series and the constant coefficients for these terms will vary with each tissue and tissue blood flow range. This is to ensure the best possible linear relation between the blood flow image algorithm and tissue blood flow. For example, using only the zero and first order terms in the series are typical, however, the zero and second order terms, or zero, first, and second order terms could also be used if an empirical analysis shows this to provide a better linear blood flow relation. (It should be noted that the zero order term is used to remove the inherent instrument offset for tissue having no blood flow.)

Equations 2, 4 and 5 represent a temporal and spatial comparison on a population of speckles for a given region within a reference image and a captured sequence of speckle images. The independent variables i, j, and $N_{MAX}$ are equation parameters chosen by the operator to reflect the desired quality of the blood flow calculations balanced with the quality of the image detail and temporal response of the instrument. For example, the statistics of the comparison between the reference image and the speckle images is improved by increasing the number of speckles analyzed. A larger number of speckles are achieved by increasing i and j or $N_{MAX}$.

For a maximum detail in blood flow images i and j can be set to zero and a strict first order comparison of temporal speckles is performed. This would be used if the physician requires capturing a blood flow image at the highest possible detail to analyze tissue microvascular structure. A larger capture sequence requires a longer time between successive blood flow images but a reasonable blood flow image can be produced using a value of $N_{MAX}$ equal to 20.

The methods for analyzing temporal speckles to generate blood flow images that exist in the prior art quantify blood flow by measuring the differences in intensity of individual speckles in successive scans. This analysis is a time differentiated technique rather than our time integrated method and requires a high-speed capturing device that is limited to a lower resolution (Fujii, 1987; Fukuoka, 1999; Fukuoka, 1999; and U.S. Pat. Nos. 4,862,894, 5,163,437 and 5,240,006). These time differentiation methods can also lead to erroneous measurements because of the finite capture time imposed by a time integrating capturing device such as a CCD (Konishi and Fujii, 1995; Tamaki, et al, 1994).

For a maximum blood flow video frame rate $N_{MAX}$ can be set to one and a strict first order comparison of the spatial speckle population is performed. This would be used if the physician wants to observe high frequency blood flow fluctuations within the tissue of interest. Larger values of i and j will also smooth out image details such as anatomical margins and boundaries but a reasonable blood flow image can be produced using a value of 2 or 3 for both i and j.

Methods for analyzing spatial structures within laser speckle images that exist in prior art use a statistical contrast calculation on the speckle population within an analysis window that results in a considerable reduction in the resolution of the final blood flow image compared to that of the captured speckle image (Briers, 1999; Briers and Webster, 1995; Dunn et al, 2001). An exemplary method disclosed in this patent maintains the image pixel resolution and optical field of view between the laser speckle image and the generated blood flow image. In this way, a one to one pixel correlation between a live video feed of the speckle images and the blood flow image is possible. This is desirable for an effective clinical instrument designed for endoscopic applications.

Prior art spatial analysis techniques are also limited to producing speckle contrast images that have a non-linear relation with tissue blood flow (Briers, 1999; Briers and Webster, 1995).

The combined spatial and temporal comparison algorithm (equations 2, 4 and 5) with the user defined spatial/temporal comparison parameters (i, j, and $N_{MAX}$) make the endoscopic instrument a more versatile clinical tool because the operator is free to decide on the desired resolution and the acceptable signal to noise ratios for any given physiological or clinical measurement.

To improve the image quality and reduce noise, a software averaging of several blood flow images is available. This method can also be used to average out unwanted pulsatile frequencies that may be present in the flow if measurement of only low frequency blood flow change is desired. The average calculation is given by;

$$I_{BF,AVERAGE}(x, y) = \sum_{n=1}^{n_{MAX}} I_{BF,n}(x, y), \quad (6)$$

where $I_{BF,n}(x,y)$ represents the intensity of the (x,y) pixel in the $n^{th}$ blood flow image for a sequence of $n_{MAX}$ blood flow images.

In a clinical setting, relative motion between the patient and operator can occur creating what is known in the field of blood perfusion measurement as "motion artifact". Motion artifact will add to the destruction of speckle in the captured speckle images, giving a positive offset in the final blood flow images. This artifact can be eliminated by holding both the patient and instrument fixed during image capture. However, in a clinical setting this is difficult to achieve. Therefore, for an effective clinical LSI instrument, it is important to determine when motion artifact occurs during image capture and discard those images from blood flow calculations.

An exemplary and preferred method for reducing motion artifact in flow or motion measurement is now presented.

FIG. 4 demonstrates an exemplary method disclosed in this patent to determine if patient/operator artifact motion occurs during capture of a speckle image.

Motion artifact can be determined by analyzing stationary "target" areas within a captured speckle image. These stationary target areas should represent a well-contrasted speckle pattern and sometimes appear naturally within the image. For example, the camera field of view 26 normally contains an area containing various tissue types surrounding the specific tissue of interest 10. If one of these tissue types is a tissue known to contain minimal flow 24, such as cartilage, then the image region containing this tissue is specified as a target region. If a minimal flow target cannot be identified within the camera field of view then a special probe 25 containing a target cell 27 is placed within the camera field of view 26 next to the tissue of interest 10. The target cell comprises a flat painted metal surface of average surface roughness greater than one wavelength, producing a well-contrasted speckle pattern.

Various methods can be used to analyze the speckle structure within the target region to determine if motion artifact occurs. These methods require determining an average value for the pixels within the defined region and evaluating the minimum sum of difference value for each pixel and the associated average value to evaluate the speckle structure over the illuminated target region. For a stationary target with zero flow the sum of difference value is at a maximum. This maximum depends on characteristics of the light source (polarization and modal quality) and tissue and must be determined in a calibration measurement that is performed when little or no motion is occurring. When motion artifact occurs the speckle structure over the target becomes destroyed and the sum of difference value decreases, approaching zero.

The various motion artifact detection methods require 6 basic steps:

1) Identifying a stationary target tissue 24 within the camera field of view or, in the absence of any stationary tissue, probe 25 containing the target cell 27 is placed within the camera field of view and identified within the image.
2) Capturing a speckle image containing the tissue of interest and the stationary target.
3) Defining the region of pixels within the image containing the target.
4) Generating an average intensity value for the pixels within the defined region.
5) Determining the level of destruction in speckle structure as a result of relative motion by performing a sum of difference calculation on the defined region of pixels within the captured speckle image and the average intensity value for those pixels.
6) Discarding speckle images where the sum of difference value falls below a specified minimum, where such minimum represents the tolerance value specified by the operator for motion artifact that destroys the speckle pattern within a given image.
7) Determining a specified minimum value from a calibration procedure that consists of capturing a speckle image in the absence of motion and determining the sum of difference value for the target region and adjusting this value to include a specified tolerance range.

Variations on generating the average intensity value and sum of difference calculation in the measurement and calibration procedure may be used. An average intensity value used in step 4 can be determined specifically for each pixel within the defined region by generating a reference image from the captured speckle image $$I_{REF}(x, y) = \frac{1}{(2i+1)} \sum_{x-i}^{x+i} \left( \frac{1}{(2j+1)} \sum_{y-j}^{y+j} I_{SP}(x, y) \right), \quad (7)$$

where equation 2 was used with $N_{MAX}$ set to one. The sum of difference calculation in step 5 is then performed between the captured speckle image and the generated reference image for the pixels within the target region $$TARGET_{SD} = \sum_{pixels} |I_{SP}(x, y) - I_{REF}(x, y)|, \quad (8)$$

where $TARGET_{SD}$ represents the sum of differences of the (x,y) pixels in the captured speckle image, $I_{SP}$, and the generated reference image, $I_{REF}$, within the target region and summation is performed over all pixels within the defined region.

Alternatively, an average intensity value, $I_{AVG}$, is determined for all pixels within the entire analysis region $$I_{AVG} = \left( \frac{1}{number} \right) \sum_{pixels} I(x, y), \quad (9)$$

where I(x,y) is the intensity of pixel (x, y) contained within the region, number is the number of pixels within the defined region, and summation is performed over all pixels within the region. The sum of difference value in step 5 is then determined using the normalized sum of difference, $REGION_{SD}$, of all pixels within the region and the calculated average intensity value $$REGION_{SD} = \left( \frac{1}{I_{AVG}} \right) \sum_{pixels} |I(x, y) - I_{AVG}|. \quad (10)$$

It is sometimes difficult to ensure that motion does not occur during the calibration procedure for determining the minimum sum of difference value. Therefore, this process can be automated using a software routine that captures a sequence of speckle images. The sum of difference value within the target region of each speckle image can be calculated and the minimum or average value of the entire sequence can be used as the target minimum value for step 6. This minimum value can then be adjusted by adding a specified offset to enable a tolerance level to the blood flow measurement. This tolerance level depicts a balance between waiting a long time to capture a blood flow image with absolutely no motion and decreasing the length of time by allowing a moderate amount of motion artifact.

Once the minimum value is calibrated and determined for a particular setup the value can be stored in a look up table for future reference. Using this minimum target value, each speckle image that is captured is analyzed within the specified target region to determine if the target sum of difference value falls below the minimum target value. When the target sum of difference value falls below the minimum, speckle images are immediately discarded before blood flow calculations are performed and a warning is given to the operator that motion artifact has occurred.

This motion artifact feature should be used for endoscopic surgery as relative motion between the patient and surgeon can easily occur during capture of a laser speckle image.

The noise reduction techniques in this instrument are unique from prior art and the specific methods are desirable for endoscopic applications in which some amount of patient/operator motion will inevitably be present.

A person skilled in the art could make immaterial modifications to the invention described and claimed in this patent without departing from the essence of the invention. For example, new endoscopic systems use digital cameras, where digitization of CCD signals is performed within the camera system rather than on a frame grabber card. These digitized images are transferred along digital transfer cables rather than standard analog video signal cables and a direct connection to the computer processing system bus is possible circumventing the need for a frame grabber card. Also, we have presented only two of the possible methods of laser light delivery to the tissue. One method uses the endoscope's internal light guide, easily conforming to standard endoscopic procedures. The alternate method requires a custom light guide, external to the standard endoscopic shaft containing the relay lens system and internal light guide. This method requires minor modifications to the endoscopic probe but provides better quality blood flow measurements.

What is claimed is:

1. An apparatus for the endoscopic measurement of motion within an enclosed cavity, comprising:
   an electro-magnetic radiation source;
   a guide for guiding electro-magnetic radiation from the electro-magnetic radiation source down an endoscopic device to illuminate a target containing motion within an enclosed cavity;
   an electro-magnetic radiation receiving system containing an optical arrangement for endoscopically relaying an image of a two-dimentional region of the target onto a two-dimentional detector array, the image of the target containing speckle structure information;
   a capture device for capturing the image of the target from the electro-magnetic radiation receiving system; and
   a processing device connected to the capture device for calculating motion information from speckle structure information in the captured image.

2. The apparatus of claim 1, wherein said processing device operates on the speckle structure information to generate images of motion.

3. The apparatus of claim 1, further comprising a display connected to one of the electro-magnetic radiation receiving system, the capture device and the processing device for the immediate visual display of two-dimensional color-coded images representing various regions containing different levels of motion.

4. The apparatus of claim 1, wherein said processing device is adapted for:
   capturing a sequence of speckle images of laser illuminated tissue;
   comparing these speckle images to a reference image that is an image of the illuminated tissue where speckle has been reduced; and
   representing information obtained from this comparison in image format such that images are generated with a relation to blood flow.

5. The apparatus of claim 4, in which the processing device is adapted for capturing a reference image that is similar to the speckle images of laser illuminated tissue but with reduced speckle structure by illuminating the tissue with a light source of reduced coherence.

6. The apparatus of claim 4, in which the processing device is adapted for reducing speckle within the captured speckle images of laser illuminated tissue, $I_{SP,N}$, to generate a reference image, $I_{REF}$, where $$I_{REF}(x, y) = \frac{1}{N_{MAX}} \sum_{N=1}^{N_{MAX}} \left[ \frac{1}{(2i+1)} \sum_{x-i}^{x+i} \left( \frac{1}{(2j+1)} \sum_{y-j}^{y+j} I_{SP,N}(x, y) \right) \right]$$

and represents the intensity of the (x,y) pixel in the generated reference image and $I_{SP,N}$ (x,y) represents the intensity of the (x,y) pixel in the $N^{th}$ speckle image of the captured sequence of $N_{MAX}$ speckle images, i and j represent the boundaries for a chosen region of pixels surrounding the (x,y) pixel.

7. The apparatus of claim 4, in which the processing device is adapted for comparing the speckle images with the reference image, by:
   determining the sum of difference between the pixels in the speckle images and the reference image using the calculation;

$$I_{SD}(x, y) = \sum_{N=1}^{N_{MAX}} \left[ \sum_{x-i}^{x+i} \left( \sum_{y-j}^{y+j} |I_{SP,N}(x, y) - I_{REF}(x, y)| \right) \right],$$

where $I_{REF}$ (x,y), $I_{SP,N}$ (x,y) and $I_{SD}$ (x,y) represent the intensity of the (x,y) pixel in the reference image, the $N^{th}$ speckle image and the generated sum of difference image, respectively. i and j represent the boundaries for a chosen region of pixels surrounding the (x,y) pixel; and
   generating a blood flow image from the reference and sum of difference images using the following calculation;

$$I_{BF}(x, y) = \sum_{C=0}^{C_{MAX}} A_C \left( \frac{I_{REF}(x, y)}{I_{SD}(x, y)} \right)^C$$

where $I_{BF}$ (x,y) represents the intensity of the (x,y) pixel in the blood flow image, C represents the order of terms in the power series of highest order $C_{MAX}$ of the independent variable that is the ratio of $I_{REF}$ (x,y), and $I_{SD}$ (x,y), and $A_C$ is the coefficient for each term.

8. The apparatus of claim 4 in which the processing device is configured for eliminating motion artifact in the blood flow images by evaluating the speckle structure of laser light reflected from a stationary target located within the field of view of a captured speckle image.

9. The apparatus of claim 4 in which the processing device is configured for eliminating motion artifact in blood flow images by: 1) using a stationary target containing a well-contrasted speckle pattern within the illuminated region, 2) capturing a speckle image containing the tissue of interest and the stationary target, 3) defining a region of pixels within the image containing the stationary target, 4) determining the average pixel intensity, $I_{AVG}$, for all pixels contained within the defined region $$I_{AVG} = \left( \frac{1}{number} \right) \sum_{pixels} I(x, y),$$

where I(x,y) is the intensity of pixel (x,y) contained within the region of pixels, "number" is to number of pixels within the region, and the summation is performed over all pixels within the region, 5) determining the normalized sum of difference, $REGION_{SD}$, of all pixels within the region using the calculated average intensity $$REGION_{SD} = \left( \frac{1}{I_{AVG}} \right) \sum_{pixels} |I(x, y) - I_{AVG}|$$

and, 6) discarding speckle images where the $REGION_{SD}$ value falls below a specified minimum, where such minimum represents the tolerance value specified by the operator for motion artifact that destroys the speckle pattern within a given image.

10. The apparatus of claim 1, further comprising a display connected to one of the electro-magnetic radiation receiving system, the capture device and the processing device for the immediate visual display of captured two-dimensional images of the illuminated target.

11. The apparatus in claim 1, wherein said apparatus is adapted for the detection of motion, where the motion comprises the flow of blood within an illuminated tissue enclosed within a body cavity.

12. The apparatus of claim 1 in which the electromagnetic radiation source is a laser and further comprising a source of white light coupled to the guide for producing video images of the target.

13. The apparatus of claim 12 in which the processing device is arranged to produce blood flow images having a one-to-one pixel correspondence with the video images.

14. The apparatus of claim 1 in which the motion information comprises blood flow images linearly related to tissue blood flow.

15. A method of detecting motion comprising the steps of:
capturing a sequence of speckle images of a laser illuminated target;
comparing the speckle images to a reference image that is an image of the illuminated target where speckle has been reduced; and
representing information obtained from this comparison in image format such that images are generated with a relation to motion.

16. The method of claim 15 further comprising capturing a reference image that is similar to the speckle images of the laser illuminated target but with reduced speckle structure by illuminating the target with a light source of reduced coherence.

17. The method of claim 15 further comprising a software method for reducing speckle within the captured speckle images of a laser illuminated target, $I_{SP,N}$, to generate a reference image, $I_{REF}$, where $$I_{REF}(x,y) = \frac{1}{N_{MAX}} \sum_{N=1}^{N_{MAX}} \left[ \frac{1}{(2i+1)} \sum_{x-i}^{x+i} \left( \frac{1}{(2j+1)} \sum_{y-j}^{y+j} I_{SP,N}(x,y) \right) \right]$$

and represents the intensity of the (x,y) pixel in the generated reference image and $I_{SP,N}$ (x,y) represents the intensity of the (x,y) pixel in the $N^{th}$ speckle image of the captured sequence of $N_{MAX}$ speckle images i and j represent the boundaries for a chosen region of pixels surrounding the (x,y) pixel.

18. The method of claim 15, in which the method for generating images containing motion information further comprises a software method for comparing the speckle images with the reference image, where such method consists of:
determining the sum of difference between the pixels in the speckle images and the reference image using the calculation;

$$I_{SD}(x,y) = \sum_{N=1}^{N_{MAX}} \left[ \sum_{x-i}^{x+i} \left( \sum_{y-j}^{y+j} |I_{SP,N}(x,y) - I_{REF}(x,y)| \right) \right],$$

where $I_{REF}$ (x,y), $I_{SP,N}$ (x,y) and $I_{SD}$ (x,y) represent the intensity of the (x,y) pixel in the reference image, the $N^{th}$ speckle image and the generated sum of difference image, respectively i and j represent the boundaries for a chosen region of pixels surrounding the (x,y) pixel; and generating a motion image from the reference and sum of difference images using the following calculation;

$$I_{Motion}(x,y) = \sum_{C=0}^{C_{MAX}} A_C \left( \frac{I_{REF}(x,y)}{I_{SD}(x,y)} \right)^C$$

where $I_{Motion}$ (x,y) represents the intensity of the (x,y) pixel in the motion image, C represents the order of terms in the power series of highest order $C_{MAX}$ of the independent variable that is the ratio of $I_{REF}$ (x,y), and $I_{SD}$ (x,y), and $A_C$ is the coefficient for each term.

19. The method of claim 15 further comprising eliminating motion artifact in the motion images by evaluating the speckle structure of laser light reflected from a stationary target located within the field of view of a captured speckle image.

20. The method of claim 15 further comprising eliminating motion artifact in motion images by: 1) using a stationary target containing a well-contrasted speckle pattern within the illuminated region, 2) capturing a speckle image containing the target of interest and the stationary target, 3) defining a region of pixels within the image containing the stationary target, 4) determining the average pixel intensity, $I_{AVG}$, for all pixels contained within the defined region $$I_{AVG} = \left( \frac{1}{number} \right) \sum_{pixels} I(x,y),$$

where I(x,y) is the intensity of pixel (x, y) contained within the region of pixels, "number" is the number of pixels within the region, and the summation is performed over all pixels within the region, 5) determining the normalized sum of difference, $REGION_{SD}$, of all pixels within the region using the calculated average intensity $$REGION_{SD} = \left( \frac{1}{I_{AVG}} \right) \sum_{pixels} |I(x,y) - I_{AVG}|$$

and, 6) discarding speckle images where the $REGION_{SD}$ value falls below a specified minimum, where such minimum represents the tolerance value specified by the operator for motion artifact that destroys the speckle pattern within a given image.

21. The method of claim 15, where the motion comprises the flow of blood within an illuminated tissue forming the laser illuminated target.

* * * * *